US011293843B2

(12) United States Patent
Pugia et al.

(10) Patent No.: US 11,293,843 B2
(45) Date of Patent: Apr. 5, 2022

(54) PARTICLE RELEASE AND COLLECTION

(71) Applicant: SIEMENS HEALTHCARE DIAGNOSTICS INC., Tarrytown, NY (US)

(72) Inventors: Michael Pugia, Granger, IN (US); Karen L. Marfurt, Edwardsburg, MI (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 399 days.

(21) Appl. No.: 14/891,423

(22) PCT Filed: May 13, 2014

(86) PCT No.: PCT/US2014/037920
§ 371 (c)(1),
(2) Date: Nov. 16, 2015

(87) PCT Pub. No.: WO2014/186411
PCT Pub. Date: Nov. 20, 2014

(65) Prior Publication Data
US 2016/0123852 A1 May 5, 2016

Related U.S. Application Data

(60) Provisional application No. 61/824,816, filed on May 17, 2013.

(51) Int. Cl.
| | | |
|---|---|---|
| *G01N 1/30* | (2006.01) | |
| *G01N 33/50* | (2006.01) | |
| *C12Q 1/24* | (2006.01) | |
| *C12Q 1/6806* | (2018.01) | |

(52) U.S. Cl.
CPC ............... *G01N 1/30* (2013.01); *C12Q 1/24* (2013.01); *C12Q 1/6806* (2013.01); *G01N 33/5005* (2013.01)

(58) Field of Classification Search
CPC .......... C12Q 1/24; C12Q 1/6806; G01N 1/30; G01N 33/5005
See application file for complete search history.

(56) References Cited

U.S. PATENT DOCUMENTS

| | | | | |
|---|---|---|---|---|
| 3,558,066 A | * | 1/1971 | Alliger .............. | A61K 41/0028 241/2 |
| 4,666,595 A | * | 5/1987 | Graham ............... | B03C 1/032 210/222 |
| 5,256,571 A | * | 10/1993 | Hurley .............. | A01N 1/02 435/1.1 |
| 6,265,229 B1 | | 7/2001 | Fodstad et al. | |
| 6,303,375 B1 | * | 10/2001 | Kimura ............... | C12M 25/14 435/177 |
| 6,719,449 B1 | * | 4/2004 | Laugharn, Jr. ........ | B01F 11/02 366/127 |
| 6,794,141 B2 | * | 9/2004 | Erlander ............. | C12Q 1/6865 435/6.14 |
| 6,949,355 B2 | | 9/2005 | Yamanishi et al. | |
| 7,166,443 B2 | | 1/2007 | Walker et al. | |
| 7,232,653 B1 | | 6/2007 | Walker et al. | |

FOREIGN PATENT DOCUMENTS

WO    2008107652    12/2008

OTHER PUBLICATIONS

Guo et al. "Ultrasound-induced release of micropallets with cells" (2012), Applied Physics Letters, vol. 101, No. 163703: 1-3 (Year: 2012).*
Lee et al. "Three-Dimensional Cell Culture Matrices: State of the Art" (2008), Tissue Engineering, Part B, vol. 14, No. 1: 61-86 (Year: 2008).*
Radbruch et al. "Detection and isolation of rare cells" (1995), Current Opinion in Immunology, vol. 7: 270-273. (Year: 1995).*
Liu et al. "Selective Individual Primary Cell Capture Using Locally Biofunctionalized Micropores", Mar. 1, 2013, PLoS One, vol. 8: 3, e57717, pp. 1-(Year: 2013).*
Azioune et al. "Simple and rapid process for single cell micro-patterning" (2009), Lab on a Chip, vol. 9: 1640-1642. (Year: 2009).*
Gunn et al. "Micropallet Technology for Investigating Tumor Cellular Profiles and Analysis of Rare Cell Subsets" (2008), Proceedings of BioMed, 3rd Frontiers in Biomedical Devices Conferences, Jun. 18-20. (Year: 2008).*
Frank A. W. Coumans et al: "Filtration Parameters Influencing Circulating Tumor Cell Enrichment from Whole Blood", PLOS One, vol. 8, No. 4, p. e61774, (2013).
Juang R-S et al: "Flux recovery in the ultrafiltration of suspended solutions with ultrasound", Journal of Membrane Science, Elsevier BV, NL, vol. 243, No. 1-2, pp. 115-124, (2004).
International Search Report for PCT/US2014/037920, dated Sep. 15, 2014.

* cited by examiner

*Primary Examiner* — Teresa E Knight

(57) ABSTRACT

Particles are released from a particle-containing area of a first surface of a porous matrix. The particle-containing area is contacted with a liquid medium and sonic energy is applied to an opposing area on a second surface of the porous matrix, wherein the opposing area is opposite to the particle-containing area. The particles may be biological particles or non-biological particles.

21 Claims, 2 Drawing Sheets

PARTICLE RELEASE AND COLLECTION

CROSS-REFERENCE TO RELATED APPLICATIONS

This application claims priority to U.S. Provisional Application Ser. No. 61/824,816 filed May 17, 2013, which is incorporated herein by reference in its entirety.

BACKGROUND

The invention relates to methods for releasing and collecting particles such as biological particles from a surface of a porous matrix. More particularly, the invention relates to methods for separately releasing and collecting biological particles from different populations of biological particles that are present on a surface of a porous matrix.

Cellular analysis is important in medical applications such as, for example, diagnosis of many diseases. However, many medical applications of cellular analysis require isolation of certain cells of interest, which typically represent only a small fraction of a sample under analysis. For example, circulating tumor cells ("CTCs") are of particular interest in the diagnosis of metastatic cancers. In conventional methods, CTC are isolated from whole blood by first removing red blood cells (RBCs) by lyses. In a 10 mL blood sample, a few hundred CTCs are to be separated from about 800,000,000 white blood cells ("WBCs"). Therefore, methods with high separation efficiency and cell recovery rates are necessary.

For rare cells such as, for example, CTCs to be analyzed by conventional scanning microscopy methods or molecular methods such as next generation sequencing, normal cells or non-rare cells (typically, WBCs and RBCs) must be reduced to a ratio of about 200 WBCs to 1 rare cell and the sample volume must be reduced from about 10 ml to a few hundred microliters.

Several approaches have been developed to date to capture, isolate and enrich rare cells such as, for example, CTCs. One approach is to deplete WBCs from a whole blood sample, a process referred to as negative depletion. Another approach is to enrich CTCs in a whole blood sample, a process referred to as positive enrichment. Both of the above approaches may rely on a variety of techniques such as, for example, magnetic particle separation, filtration, flow cytometry, cell sorting techniques, centrifugation, and separation using microfluidic channels and chambers, to conduct the rare cell analysis.

For example, separation using microfluidic channels and chambers has been applied to separate specific types of cells from a bulk fluid sample by using a principle of surface adhesion in a capillary gap (see, for example, U.S. Pat. No. 7,094,354, the entire disclosure of which is incorporated herein by reference). This principle of surface adhesion relies on adjusting the surface energy of a microfluidic chip surface relative to the surface energy of the bulk fluid and the cells of interest. Cells will adhere to higher energy surfaces (hydrophilic surfaces) in a capillary gap when the ratio of the gap height to the diameter of the cell is in a range from about 5/1 to about 100/1.

Cell filtration for the separation of cancer cells using a porous matrix is used to sort cells by size and, in most instances, such filtration methods allow for the extraction of cells following separation. Both microfluidic post and microfluidic membrane methods are used in these filtration approaches. However, the existing filtration methods are limited by certain factors, which include, for example, the range of diameters that in vitro cells have rather than a single diameter. This range of diameters is demonstrated, for example, in the case of cancer cell populations and white blood cell populations, which have overlapping diameters. During filtration small cancer cells are lost and larger white blood cells contaminate the separated material. Furthermore, cancer cell populations and white blood cell populations are very heterogeneous and comprise a variety of cell diameter types within these individual populations. For example, the range of diameters for white blood cells is much wider when considering samples including populations of neutrophils, eosinophils, basophils, macrophages, lymphocytes and macrophages. Cancer cells in blood can also range in size.

In addition, blood cells are typically fixed before separation by filtration to improve separation of the cells. Recovery of target cells is reduced when fixation is not used since some target cells have higher deformability than other target cells. Fixation causes all cells to have similar deformability (viscoelastic properties). However, there are a number of disadvantages to fixing cells such as, for example, the requirement of greater pressure for passage of the fixed cells through a porous matrix. As pressure increases, ideal pore size decreases. Smaller pores lead to greater capture of undesired cells. Another disadvantage is that fixed cells are not viable and cannot be grown or used to measure cells responses to stimulus.

There is, therefore, a need to develop a method of cell removal from membranes that is facile and that does not require fixation of cells. The method should improve cell recovery and be independent of differences in cell diameter and differences in viscoelastic properties and should be equally successful for fixed and non-fixed cells.

SUMMARY

Some examples in accordance with the principles described herein are directed to methods of releasing particles from a particle-containing area of a first surface of a matrix. The method comprises contacting the particle-containing area with a liquid medium and applying sonic energy to an opposing area on a second surface of the matrix to release the particles, wherein the opposing area is opposite to the particle-containing area. The particles may be biological particles or non-biological particles.

Some examples in accordance with the principles described herein are directed to methods of releasing biological particles from a biological particle-containing area of a first surface of a porous matrix. The method comprises contacting the biological particle-containing area with a liquid medium and applying sonic energy to an opposing area on a second surface of the porous matrix to release the biological particles, wherein the opposing area is opposite to the biological particle-containing area.

Some examples in accordance with the principles described herein are directed to methods of selectively collecting a population of biological particles from a surface of a porous matrix comprising different biological particle populations. For each different biological particle population to be collected, sonic energy is applied to an area on a first surface of the porous matrix. The area, to which the sonic energy is applied, is opposite to an area on a second surface of the porous matrix wherein the area on the second surface comprises the population of biological particles. The biological particles of the population of biological particles are collected from the area on the second surface into a liquid medium in contact with the area on the second surface.

Some examples in accordance with the principles described herein are directed to methods of selectively collecting a population of cells from a surface of a porous matrix comprising different cell populations. For each different cell population to be collected, sonic energy having a frequency of about 20 kilohertz (kHz) to about 200 megahertz (MHz) is applied to an area on a first surface of the porous matrix wherein the area is opposite to an area on a second surface of the porous matrix. The area on the second surface is identified as comprising a population of cells. A pore size of the porous matrix is about 1 µm to about 100 µm. Cells of the population of cells are collected from the area on the second surface into an aqueous buffered medium in contact with the area on the second surface. The porous matrix is disposed over a container that contains the aqueous buffered medium.

BRIEF DESCRIPTION OF THE DRAWINGS

The drawings provided herein are not to scale and are provided for the purpose of facilitating the understanding of certain examples in accordance with the principles described herein and are provided by way of illustration and not limitation on the scope of the appended claims.

DETAILED DESCRIPTION OF SPECIFIC EMBODIMENTS

General Discussion

Examples in accordance with the principles described herein use sonic energy applied to a back side of a matrix to allow substantially complete removal of certain particles such as biological particles from an area on a front side of the matrix, which area is opposite to the area to which the sonic energy is applied. The phrase "substantially complete removal" means that at least 90%, or at least 95%, or at least 99%, or 100% of the particles are disengaged from the matrix and collected. Removal is accomplished with minimal removal time and minimal damage to the particles including biological markers on the particles. In some examples, sonic energy is applied to an opposing area on a surface of the matrix. The phrase "opposing area" refers to the area on one surface of a matrix that is opposite to the area on an opposite surface of the matrix that contains the biological particles. The area to which the sonic energy is applied corresponds to an opposing area of the matrix where the particles to be removed are found. The particles are collected from the matrix into a liquid medium in contact with the area where the particles to be removed are found.

The matrix may be a porous or non-porous, solid or semi-solid material and may be comprised of an organic or inorganic, water insoluble material. The matrix can have any of a number of shapes such as, for example, tubular (e.g., hollow fiber, spiral wound, or hollow fine fiber), track-etched, or planar or flat surface (e.g., strip, disk, film, membrane, BioMEMS (Biomicroelectromechanical System) membrane slide, microfluidic filter, or plate). The matrix may be fabricated from a wide variety of materials, which may be naturally occurring or synthetic, polymeric or non-polymeric, fibrous or non-fibrous. Examples, by way of illustration and not limitation, of such materials for fabricating a porous matrix include polymeric materials including, but not limited to, cellulose (including paper), nitrocellulose, cellulose acetate, polycarbonate, poly (vinyl chloride), polyacrylamide, polyacrylate, polyethylene, polypropylene, poly-(4-methylbutene), polystyrene, polymethacrylate, poly(ethylene terephthalate), nylon, poly(vinyl butyrate), and poly(p-xylylene), e.g., PARALYENE® polymers; and non-polymeric materials including, but not limited to, ceramic material, metallic material, for example, either used by themselves or in conjunction with one another and/or with other materials.

In some examples in accordance with the principles described herein, the matrix is a porous matrix that is circular in shape and has a diameter of about 10 millimeters (mm) to about 50 mm and a plurality of pores of about 2 microns (µm) to about 1000 µm, or in some examples, about 5 µm to about 20 µm.

In some examples in accordance with the principles described herein, two or more different biological particle, e.g., cell, populations are selectively removed and collected from a surface of a matrix. Populations of different biological particles are first collected onto a surface of a matrix prior to their selective removal. For example, a sample containing different cells is passed through a matrix that is porous whereby populations of different cell types are collected on a surface of the porous matrix. The surface of the matrix has regions where various populations of different cells are collected. While not required, the locations of specific cell types can be determined by image analysis of cells or some other analytic technique. The surface of the matrix with biological particles is disposed over a container that contains a liquid medium or collection medium, which may be, for example, an aqueous buffered medium. The population of biological particles is collected from the surface into the collection medium in contact with the surface on which the biological particles were initially collected.

The application of sonic energy to a specific area of the matrix is used to separately remove and collect biological particles for each of the different biological particle populations identified to be present on the matrix. For each different biological particle population to be collected, sonic energy having a frequency of about 20 kHz to 200 MHz is applied to an area on the opposing surface of the matrix. Sonic energy can be applied to the entire opposing surface to remove all biological particles. Alternatively, sonic energy can be applied to the locations of specific biological particle types and only those biological particles removed and collected.

In some examples, sonic energy is applied to a first opposing area on the surface of the matrix where the first opposing area corresponds to an area on an opposite surface of the matrix that contains a first biological particle population to be removed and collected. The biological particles of the first biological particle population are collected into a liquid medium in contact with the area of the surface of the matrix that contains the first biological particle population. Sonic energy is then applied to a second opposing area on the surface of the matrix where the second opposing area corresponds to an area on an opposite surface of the matrix that contains a second biological particle population to be removed and collected. The biological particles of the second biological particle population are collected into a liquid medium in contact with the area of the surface of the matrix that contains the second biological particle population. The steps of applying sonic energy to an opposing area on the surface of the porous matrix and collecting biological particles into a medium are repeated for each of the different biological particle populations present on the matrix. Alternatively, sonic energy may be applied simultaneously to two or more different opposing areas on the surface of the matrix to remove and collect two or more biological particle populations into the same collection medium rather than removing and collecting each different biological particle population separately. In some examples, there may be areas of the surface of the matrix that comprise cells of interest and other areas where the cells are not of particular interest. If a sample is enriched in cells of interest to an acceptable level, all cells can be removed from the matrix. On the other hand, if sample is not enriched to an acceptable, different cell populations may be removed by separate application of sonic energy in accordance with the principles described herein.

The separation of biological particles such as, e.g., cells, of one biological particle population from biological particles of another biological particle population is achieved in accordance with the principles described herein and is independent of the viscoelastic properties of the biological particles and of the diameter of the biological particles. Furthermore, the methods in accordance with the principles described herein work for fixed and non-fixed live biological particles.

Methods in accordance with the principles described herein have application to any technique that involves the collection of particles such as biological particles, e.g., cells, on a matrix. In many instances, the techniques include, but are not limited to, filtration, microfluidic techniques, and blood smear techniques, for example. Any of a number of filtration techniques may be employed to carry out contact of the blood sample with a porous matrix. Such filtration techniques include, but are not limited to, microfiltration, ultrafiltration, centrifugation, capillary flow or cross-flow filtration, for example. In some example, the porous matrix is generally part of a filtration module where the porous matrix is part of an assembly for convenient use during filtration.

Particles to be separated, removed and collected from a matrix may be present in a sample to be analyzed. The term "particles" includes biological particles such as, for example, cells, microorganisms, viruses, exosomes, casts, microemolisms, cell clusters and other particles containing cellular biological material, and non-biological particles such as, for example, fibrin, aggregates, debris, crystals, extra-cellular matrix and other components in biological fluid not containing cellular biological material. The samples may be biological samples or non-biological samples. Biological samples may be from a mammalian subject or a non-mammalian subject. Mammalian subjects may be, e.g., humans or other animal species. Biological samples include biological fluids such as whole blood, serum, plasma, sputum, lymphatic fluid, semen, vaginal mucus, feces, urine, spinal fluid, saliva, stool, cerebral spinal fluid, tears, and mucus, for example; biological tissue such as hair, skin, sections or excised tissues from organs or other body parts; for example. In many instances, the sample is whole blood, plasma or serum. Non-biological samples include, but not limited to, environmental samples such as, e.g., waste streams, rivers, lakes, landfills, streams, marshes, dirt, samples from manufacturing processes, such as culture media and bioreactors, fermentation, and processed blood samples such as apheresis and cell enrichment processes, for example.

In some examples, the particles are cells of different cell populations. In many instances the cells are rare cells, which are those cells that are present in a sample in relatively small quantities when compared to the amount of non-rare cells in a sample. In some examples, the rare cells are present in an amount of about $10^{-8}$% to about $10^{-2}$% by weight of a total cell population in a sample suspected of containing the rare cells. The rare cells may be, but are not limited to, malignant cells such as malignant neoplasms or cancer cells; circulating endothelial cells; circulating epithelial cells; fetal cells; immune cells (B cells, T cells, macrophages, NK cells, monocytes); stem cells; nucleated red blood cells (normoblasts or erythroblasts); and immature granulocytes; for example.

Non-rare cells are those cells that are present in relatively large amounts when compared to the amount of rare cells in a sample. In some examples, the non-rare cells are present in an amount of about $10^2$% to about $10^8$% by weight of a total cell population in a sample suspected of containing non-rare cells and rare cells. The non-rare cells may be, but are not limited to, white blood cells, platelets, and red blood cells, for example.

In some examples, samples are blood samples that are collected from the body of a subject into a suitable container such as, but not limited to, a bag, a bottle, a needle or a VACUTAINER® container, for example. The container may contain a medium into which the sample is delivered. The medium is usually a dry medium and may comprise an amount of platelet deactivation agent effective to achieve deactivation of platelets in the blood sample when mixed with the blood sample. The medium may also comprise one or both of an anti-coagulant and a fixing agent.

Platelet deactivation agents include, but are not limited to, chelating agents such as, for example, chelating agents that comprise a triacetic acid moiety or a salt thereof, a tetraacetic acid moiety or a salt thereof, a pentaacetic acid moiety or a salt thereof, or a hexaacetic acid moiety or a salt thereof. In some examples, the chelating agent is ethylene diamine tetraacetic acid (EDTA) and its salts or ethylene glycol tetraacetate (EGTA) and its salts. Platelet deactivation agents may also include citrate; cyclooxygenase inhibitors; adenosine diphosphate (ADP) receptor inhibitors; glycoprotein IIB/IIIA inhibitors; phosphodiesterase inhibitors; thromboxane inhibitors; and adenosine reuptake inhibitors, for example. The effective amount of platelet deactivation agent is dependent on one or more of the nature of the platelet deactivation agent, the nature of the blood sample, level of platelet activation and ionic strength, for example.

In some examples, for EDTA as the anti-platelet agent, the amount of dry EDTA in the container is that which will produce a concentration of about 1.0 to about 2.0 mg/mL of blood, or about 1.5 mg/mL of the blood. The amount of the platelet deactivation agent is that which is sufficient to achieve at least about 90%, or at least about 95%, or at least about 99% of platelet deactivation.

Anti-coagulants include, but are not limited to, Factor VII inhibitors, Factor X inhibitors, direct thrombin inhibitors, coumarins, heparin, and antithrombin proteins, for example.

Fixing agents include, but are not limited to, substances that act to cross-link proteins and/or to disable proteolytic enzymes and prevent natural generation of fibrin. In some examples, the fixing agent is an aldehyde reagent (such as, e.g., formaldehyde, glutaraldehyde, and paraformaldehyde) and ureas (such as, e.g., diazolidinyl urea or imidazolidinyl urea).

The medium into which the sample is collected may also contain one or more additional agents such as, but not limited to, $CrCl_3$ or $MnCl_2$, dextrose, glucose, citrate, adenosine triphosphate, inosine, dihydroxyacetone, 2,3-diphosphoglycerol, chloramphenicol, neomycin sulphate, magnesium chloride, iodoacetamide, sodium ascorbate, acetic acid, dimethylsulfoxide, zinc sulfate, 2-bromo-2-nitropropane-1,3-diol, urea and urea derivatives, acetamide, formamide, hydantoin, alcohols, acetic acid, formic acid, dehydrated oxidant (osmium), HEPES-glutamic acid buffer-mediated organic solvent protection effect (HOPE) (Polysciences, Inc.), diimidoester fixation agents using dimethyl suberimidate (DMS), growth factors transferrin inhibitors, and inhibitors for phosphorylation and other enzymes, for example. These additional agents, if present, are present in amounts that achieve their respective intended purposes. In some examples the medium is a standard anti-coagulant medium for collection of blood samples.

The sample such as, for example, a blood sample, either directly or after treatment to place biological particles in better form for separation by filtration, is contacted with a porous matrix such that different populations of biological particles such as, e.g., different populations rare cells are retained on the porous matrix and some or all of other biological particles such as, e.g., non-rare cells, pass through the porous matrix. As a result, a surface of the porous matrix comprises different populations of biological particles, which may be in some examples different populations of rare cells and different populations of non-rare cells.

In some examples in accordance with the principles described herein, the blood sample is diluted with a dilution medium prior to contact with the porous matrix. In some examples, the dilution medium is an aqueous medium, which may be buffered. The pH for an aqueous buffered medium is usually a moderate pH. In some examples the pH of the dilution medium is about 5 to about 8, or about 6 to about 8, or about 7 to about 8, or about 5 to about 7, or about 6 to about 7, or physiological pH, for example. Various buffers may be used to achieve the desired pH and maintain the pH during any incubation period. Illustrative buffers include, but are not limited to, borate, phosphate (e.g., phosphate buffered saline), carbonate, TRIS, barbital, PIPES, HEPES, MES, ACES, MOPS, and BICINE, for example.

The dilution medium may also comprise a lysing agent for lysing of cells. A lysing agent is a compound or mixture of compounds that disrupt the integrity of the membranes of cells thereby releasing intracellular contents of the cells. Examples of lysing agents include, but are not limited to, non-ionic detergents, anionic detergents, amphoteric detergents, low ionic strength aqueous solutions (hypotonic solutions), bacterial agents, aliphatic aldehydes, and antibodies that cause complement dependent lysis, for example. Various ancillary materials may be present in the dilution medium. All of the materials in the dilution medium are present in a concentration or amount sufficient to achieve the desired effect or function.

The amount of dilution medium combined with the blood sample is dependent on one or more of a number of factors such as, for example, the nature of the porous matrix, the nature of the blood sample, and the nature of the different populations of biological particles. In some examples in accordance with the principles described herein, the amount of dilution medium is about 5 mL to about 100 mL, or about 5 mL to about 80 mL, or about 5 mL to about 60 mL, or about 5 mL to about 50 mL, or about 5 mL to about 30 mL, or about 5 mL to about 20 mL, or about 5 mL to about 10 mL, or about 10 mL to about 100 mL, or about 10 mL to about 80 mL, or about 10 mL to about 60 mL, or about 10 mL to about 50 mL, or about 10 mL to about 30 mL, or about 10 mL to about 20 mL, or about 20 mL to about 100 mL, or about 20 mL to about 80 mL, or about 20 mL to about 60 mL, or about 20 mL to about 50 mL, or about 20 mL to about 30 mL, for example, based on 10 mL of the blood sample.

In some examples, the matrix is a porous matrix. The size of the pores of a porous matrix is that which is sufficient to preferentially retain certain biological particles while allowing the passage of other biological particles through the pores. The size of the pores of the porous matrix is dependent on the nature and size of the different populations of biological particles such as, e.g., rare cells and non-rare cells, and the pressure applied to the blood sample on the porous matrix, for example. In some examples the average size of the pores of the porous matrix is about 1 μm to about 100 μm, or about 1 μm to about 75 μm, or about 1 μm to about 50 μm, or about 1 μm to about 20 μm, or about 1 μm to about 10 μm, or about 5 μm to about 100 μm, or about 5 μm to about 75 μm, or about 5 μm to about 50 μm, or about 5 μm to about 20 μm, or about 5 μm to about 10 μm, for example. The density of pores in the porous matrix is about 1% to about 80%, or about 10% to about 80%, or about 20% to about 80%, or about 50% to about 80%, or about 20% to about 70%, for example.

In some examples in accordance with the principles described herein, pressure is applied to the blood sample on the porous matrix to facilitate passage of non-rare cells through the membrane. The level of pressure applied is dependent on one or more of the nature and size of the different populations of biological particles, the nature of the porous matrix, and the size of the pores of the porous matrix, for example. In some examples, the level of pressure applied is about 1 millibar to about 30 millibar, or about 1 millibar to about 25 millibar, or about 1 millibar to about 20 millibar, or about 1 millibar to about 15 millibar, or about 1 millibar to about 10 millibar, or about 5 millibar to about 30 millibar, or about 5 millibar to about 25 millibar, or about 5 millibar to about 20 millibar, or about 5 millibar to about 15 millibar, or about 5 millibar to about 10 millibar, for example. In some examples the pressure is an oscillating pressure, which means that the pressure is applied intermittently at regular of irregular intervals, which may be, for example, about 1 second to about 600 seconds, or about 1 second to about 500 seconds, or about 1 second to about 250 seconds, or about 1 second to about 100 seconds, or about 1 second to about 50 seconds, or about 10 seconds to about 600 seconds, or about 10 seconds to about 500 seconds, or about 10 seconds to about 250 seconds, or about 10 seconds to about 100 seconds, or about 10 seconds to about 50 seconds, or about 100 seconds to about 600 seconds, or about 100 seconds to about 500 seconds, or about 100 seconds to about 250 seconds, for example. In this approach, pressure is oscillated at about 0 millibar to about 10 millibar, or about 1 millibar to about 10 millibar, or about 1 millibar to about 7.5 millibar, or about 1 millibar to about 5.0 millibar, or about 1 millibar to about 2.5 millibar, for example, during some or all of the application of pressure to the blood sample. Oscillating pressure is achieved using an on-off switch, for example, and may be conducted automatically or manually.

Contact of the sample with the porous matrix is continued for a period of time sufficient to achieve retention of the biological particles of interest on a surface of the porous matrix to obtain a surface of the porous matrix having different populations of biological particles as discussed above. The period of time is dependent on one or more of the nature and size of the different populations of biological particles, the nature of the porous matrix, the size of the pores of the porous matrix, the level of pressure applied to the blood sample on the porous matrix, the volume to be filtered, and the surface area of the porous matrix, for example. In some examples, the period of contact is about 1 minute to about 1 hour, about 5 minutes to about 1 hour, or about 5 minutes to about 45 minutes, or about 5 minutes to about 30 minutes, or about 5 minutes to about 20 minutes, or about 5 minutes to about 10 minutes, or about 10 minutes to about 1 hour, or about 10 minutes to about 45 minutes, or about 10 minutes to about 30 minutes, or about 10 minutes to about 20 minutes, for example.

As mentioned above, some examples in accordance with the principles described herein are directed to methods of releasing particles from a particle-containing area of a first surface of a matrix. The method comprises contacting the particle-containing area with a liquid medium ("collection medium") and applying sonic energy to an opposing area on a second surface of the matrix, wherein the opposing area is opposite to the particle-containing area. In some examples, after the filtration discussed above, the surface of the matrix that contains the different cell populations is placed in contact with the liquid medium by, for example, disposing such surface over the liquid medium in a suitable container. The container may be a single container or the container may be part of a multi-container device such as, but not limited to, a multi-well device, a point of care device, a track device for automation or other configurations, for example.

In some examples, the collection medium is an aqueous medium, which may be buffered. The pH for an aqueous buffered medium is usually a moderate pH. In some examples the pH of the dilution medium is about 5 to about 8, or about 6 to about 8, or about 7 to about 8, or about 5 to about 7, or about 6 to about 7, or physiological pH, for example. Various buffers may be used to achieve the desired pH and maintain the pH during any incubation period. Illustrative buffers include, but are not limited to, borate, phosphate (e.g., phosphate buffered saline), carbonate, TRIS, barbital, PIPES, HEPES, MES, ACES, MOPS, and BICINE, for example. The aqueous medium may also contain organic solvents such as, for example, polar aprotic solvents, polar protic solvents such as, e.g., dimethylsulfoxide (DMSO), dimethylformamide (DMF), acetonitrile, an organic acid, or an alcohol, and non-polar solvents miscible with water such as, e.g., dioxene, in an amount of about 0.1% to about 50%, by volume. The temperature of the liquid medium is dependent on one or more factors such as, but not limited to, the nature of the different particle populations, the vapor pressure of the solvent, the energy of sonication, the critical micelle point, and the surface energy of the liquid, for example. In some examples, the temperature is about 4° C. to about 35° C., or about 4° C. to about 30° C., or about 4° C. to about 25° C., or about 4° C. to about 20° C., or about 4° C. to about 15° C., or about 4° C. to about 10° C., or about 10° C. to about 35° C., or about 10° C. to about 30° C., or about 10° C. to about 25° C., or about 10° C. to about 20° C., or about 10° C. to about 15° C., for example.

The collection medium may also comprise one or more surfactants, stabilizers, preservatives, and lysing agents. All of the materials in the collection medium are present in a concentration or amount sufficient to achieve the desired effect or function.

Sonic energy is then applied to a surface ("opposing surface") of the porous matrix, that is, to the surface opposite to the surface of the porous matrix that comprises the biological particles. The sonic energy may be applied to the entire opposing surface of the porous or to one or more individual areas of the opposing surface. In some examples in accordance with the principles described herein, the areas of the opposing surface to which the sonic energy is applied correspond to areas that are opposite to areas of the surface of the matrix that comprise different populations of biological particles to selectively release different populations of biological particles into a different collection medium for each different population of biological particles. The surface of the matrix comprising the population of biological particles to be released is brought into contact with a new collection medium for collecting each different population of biological particles to be released.

The term "sonic energy" refers to ultrasonic energy. A frequency of sonic energy applied is dependent on one or more factors such as, for example, the nature of the population of biological particles, the nature of the porous matrix, the pore size of the porous matrix, the nature of the collection medium, the nature of remaining non-cellular materials in the biological sample, the degree of fixation or treatment of the cells, the fragility of the biochemical material to be analyzed, the height of the probe from the surface of the matrix, and the shape of the probe, for example. The frequency of sonic energy applied is that which is sufficient to release the population of biological particles into the liquid medium in contact with the surface of the porous matrix comprising the population of biological particles. In some examples the frequency of sonic energy applied is about 20 kHz to about 200 MHz, or about 20 kHz to about 150 MHz, or about 20 kHz to about 100 MHz, or about 20 kHz to about 50 MHz, or about 50 kHz to about 200 MHz, or about 50 kHz to about 150 MHz, or about 50 kHz to about 100 MHz, or about 20 MHz to about 200 MHz, or about 20 MHz to about 150 MHz, or about 20 MHz to about 100 MHz, or about 20 MHz to about 50 MHz, or about 50 MHz to about 200 MHz, or about 50 MHz to about 150 MHz, or about 50 MHz to about 100 MHz, for example. Duration of application of sonic energy is dependent on one or more factors listed above regarding the frequency of the sonic energy applied. The duration of the application of sonic energy is that which is sufficient to release the population of biological particles into the liquid medium in contact with the surface of the porous matrix comprising the population of biological particles.

In some examples, sonic energy is applied for a period of about 1 second to about 30 minutes, or about 1 second to about 20 minutes, or about 1 second to about 10 minutes, or about 1 second to about 5 minutes, or about 30 seconds to about 30 minutes, or about 30 seconds to about 20 minutes, or about 30 seconds to about 10 minutes, or about 30 seconds to about 5 minutes, or about 1 minute to about 30 minutes, or about 1 minute to about 20 minutes, or about 1 minute to about 10 minutes, or about 1 minute to about 5 minutes, for example. In some examples the sonic energy is applied intermittently at regular of irregular intervals, which may be, for example, about 1 second to about 24 hours, or about 1 second to about 15 hours, or about 1 second to about 10 hours, or about 1 second to about 5 hours, or about 1 second to about 1 hour, or about 1 second to about 60 seconds, or about 1 second to about 30 seconds, or about 1 second to about 10 seconds, or about 30 seconds to about 600 seconds, or about 30 seconds to about 300 seconds, or about 30 seconds to about 100 seconds, or about 60 seconds to about 600 seconds, or about 60 seconds to about 300 seconds, or about 60 seconds to about 100 seconds, for example, during the above time period of application of sonic energy. Oscillation of sonic energy may be achieved using an on-off switch, for example, and may be conducted automatically or manually.

Sonic energy may be applied using a sonic energy delivering device, which comprises an aperture and a source of sonic energy in communication with the aperture. In some examples, sonic energy is generated from an electronic generator that transforms AC line power to a 20 KHz signal that drives a piezoelectric converter/transducer. This electrical signal is converted by the transducer to a mechanical vibration due to the characteristics of the internal piezoelectric crystals. The vibration is amplified and transmitted down the length of a horn (also referred to herein as a probe) where the tip longitudinally expands and contracts. The distance the tip travels is dependent on the amplitude of the power applied. Amplitude is a measurement of the excursion of the tip of the probe. Increasing the amplitude will increase the sonication intensity. The rapid vibration of the tip causes cavitation on the matrix and the liquid and the formation and violent collapse of microscopic bubbles. The collapse of thousands of cavitation bubbles releases tremendous energy in the cavitation field. The erosion and shock effect of the collapse of the cavitation bubble is the primary mechanism of fluid processing. Sonication power is measured in watts. The maximum power that is capable of being delivered will only be delivered when the resistance to the movement of the probe is high enough to draw maximum wattage. For example a 20 kHz sonicator with a one-inch diameter horn placed on a matrix is capable of reaching up to 500 Watt.

The diameter of the aperture is dependent one or more factors such as, but not limited to, the size of the area of the surface of the matrix to which sonic energy is to be applied, the frequency of the sonic energy, the nature of the population of biological particles, the nature of the matrix, the pore size of pores of a porous matrix when the matrix is porous, the nature of the collection medium, the nature of remaining non-cellular materials in the biological sample, the degree of fixation or treatment of the cells, the fragility of the biochemical material to be analyzed, the height of the probe from the surface of the matrix, and the shape of the probe, for example. The probe tip diameter dictates the amount of sample that can be effectively processed. Smaller tip diameters (microtip probes 0.063" or less) deliver high intensity sonication but the energy is focused within a small, concentrated area. Larger tip diameters can process larger volumes but offer lower intensity and require higher power. The choices of a generator and horn are matched to the size of the area on the surface of the matrix to which sonic energy is applied. The diameter of the aperture may range from about the diameter of a single cell to the diameter of the entire matrix, when the matrix is circular, or to the diameter of any sub-area of the surface of the matrix that has been identified as containing cells of interest. In some examples, the diameter of the aperture is about 10 microns (μm) to 3 centimeters (cm), or about 10 μm to about 2 cm, or about 10 μm to about 1 cm, or about 10 μm to about 0.5 cm, or about 10 μm to about 0.1 cm, or about 100 microns (μm) to 3 centimeters (cm), or about 100 μm to about 2 cm, or about 100 μm to about 1 cm, or about 100 μm to about 0.5 cm, or about 100 μm to about 0.1 cm, for example.

Figure 1:
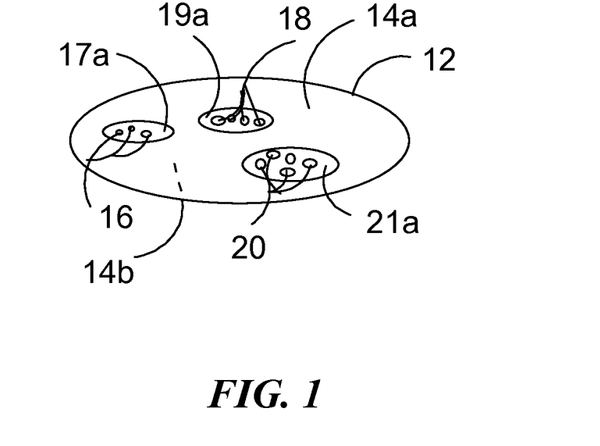
FIG. 1 is a depiction of a matrix having disposed on a surface thereof several different cell populations.

In the following description, a porous membrane is chosen as an example of a matrix and cells are chosen as an example of biological particles. Referring to FIG. 1, membrane 12 comprises surface 14a and opposing surface 14b. Surface 14a comprises population of cells 16 in area 17a, population of cells 18 in area 19a, and population of cells 20 in area 21a, each of which have been identified by means of a cell identification technique.

Figure 2:
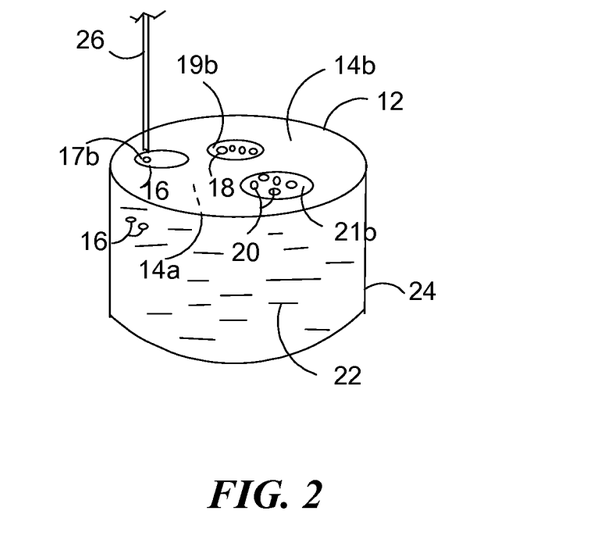
FIG. 2 is a depiction of the matrix of FIG. 1 with the matrix disposed over a container and the surface comprising the different cell populations in contact with a liquid medium. Sonic energy is applied to an area of a surface of the matrix opposite to the surface comprising the different cell populations to release cells from a cell population in an example in accordance with the principles described herein.
Figure 3:
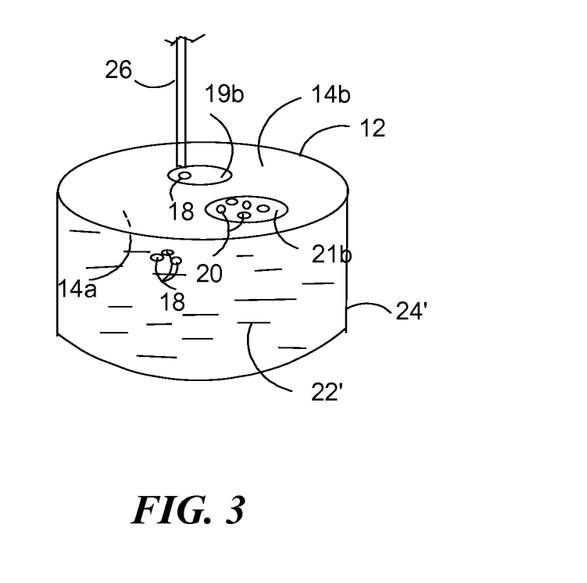
FIG. 3 is a depiction of the porous matrix of FIG. 1 with the matrix disposed over a container and the surface comprising the different cell populations in contact with a liquid medium. Sonic energy is applied to another area of the surface of the matrix opposite to the surface comprising the different cell populations to release cells from another cell population in an example in accordance with the principles described herein.
Figure 4:
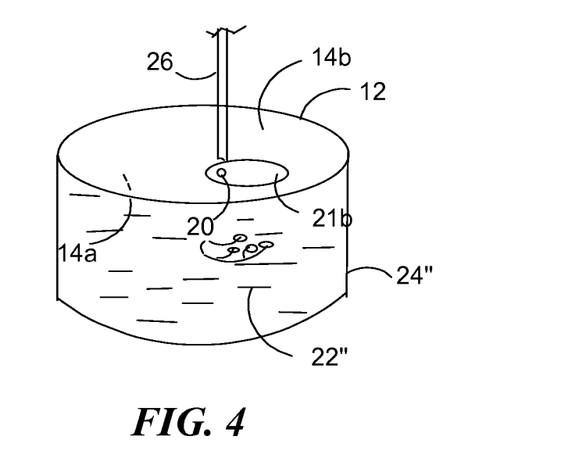
FIG. 4 is a depiction of the porous matrix of FIG. 1 with the matrix disposed over a container and the surface comprising the different cell populations in contact with a liquid medium. Sonic energy is applied to another area of the surface of the matrix opposite to the surface comprising the different cell populations to release cells from another cell population in an example in accordance with the principles described herein.

Referring to FIG. 2, surface 14a is disposed in contact with a liquid medium 22 that is contained in container 24. Sonic energy is applied by means of sonic probe 26 to area 17b on surface 14b that is opposite to area 17a on surface 14a that comprises cells 16. The frequency and duration of the sonic energy is that which is sufficient to remove cells 16 from area 17a of surface 14a of membrane 12. Cells 16 are released into liquid medium 22. Referring to FIG. 3, surface 14a is then disposed in contact with liquid medium 22' that is contained in container 24'. Liquid medium 22' may have the same or a different composition as liquid medium 22. Sonic energy is applied by means of sonic probe 26 to area 19b on surface 14b that is opposite to area 19a on surface 14a that comprises cell population 18. The frequency and duration of the sonic energy is that which is sufficient to remove cells 18 from area 19a of surface 14a of membrane 12. Cells 18 are released into liquid medium 22'. Referring to FIG. 4, the process is repeated for removal of cells 20 from area 21a into liquid medium 22" by application of sonic energy to area 21b by means of sonic probe 26.

General Description of Assay Techniques for Cell Identification on Surface of Porous Matrix As mentioned above, areas on the surface of a porous matrix that comprise different biological particle populations such as, for example, different populations of cells, may be identified by a cell identification technique. After the cells are identified, a sonic probe having a tip of suitable diameter may be employed to remove the cells from their identified location in accordance with the principles described herein. Any assay suitable for identifying cells on a surface may be employed for determining the identity of a cell. The nature of the reagents employed is dependent on the particular type of assay to be performed. The assay may be an immunoassay or a non-immunoassay. Various assay methods are discussed below by way of illustration and not limitation.

In many embodiments the reagents comprise at least one antibody specific for an antigen on the cell that is characteristic of the cell, that is, the antigen is known to be associated with the particular cell in question. This assay is generally referred to as an immunoassay as distinguished from assays that do not utilize an antibody, which are referred to as non-immunoassays. By the phrase "antibody for an antigen" is meant an antibody that binds specifically to the antigen and does not bind to any significant degree to other substances that would distort the analysis for the particular antigen.

Antibodies specific for an antigen for use in immunoassays to identify cells can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, and Fab', for example. In addition, aggregates, polymers, and conjugates of immunoglobulins or their fragments can be used where appropriate so long as binding affinity for a particular molecule is maintained.

Other reagents are included in the assay medium depending on the nature of the assay to be conducted. Such assays usually involve reactions between binding partners such as an antigen (protein) on a cell and a corresponding antibody or the binding between an antibody and a corresponding binding partner such as a second antibody that binds to the first antibody. The antibody and the antigen are members of a specific binding pair ("sbp member"), which is one of two different molecules, having an area on the surface or in a cavity, which specifically binds to and is thereby defined as complementary with a particular spatial and polar organization of the other molecule. The members of the specific binding pair will usually be members of an immunological pair such as antigen-antibody and hapten-antibody, although other specific binding pairs include, for example, biotin-avidin, hormones-hormone receptors, enzyme-substrate, nucleic acid duplexes, IgG-protein A, and polynucleotide pairs such as DNA-DNA, DNA-RNA.

As discussed above, specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules. In many embodiments of assays, preferred binding partners are antibodies and the assays are referred to as immunoassays.

In some examples by way of illustration and not limitation, the assay is an immunocytochemistry technique, a direct fluorescent antibody test or a direct immunofluorescence test.

In one example, an immunocytochemistry technique is employed to determine whether or not one or more antigens specific for respective cell populations of interest is present on the surface of the porous matrix. The cell preparation may be treated to fix the cells and to permeabilize the cells, but need not be.

Fixation of the cells immobilizes the cells and preserves cell structure and maintains the cells in a condition that closely resembles the cells in an in vivo-like condition and one in which the antigens of interest are able to be recognized by a specific antibody. The amount of fixative employed is that which preserves the cells but does not lead to erroneous results in a subsequent assay. The amount of fixative depends on one or more of the nature of the fixative and the nature of the cells, for example. In some examples, the amount of fixative is about 0.05% to about 0.15%, or about 0.05% to about 0.10%, or about 0.10% to about 0.15%, for example, by weight. Agents for carrying out fixation of the cells include, but are not limited to, cross-linking agents such as, for example, an aldehyde reagent (such as, e.g., formaldehyde, glutaraldehyde, and paraformaldehyde); an alcohol (such as, e.g., C1-C5 alcohols such as methanol, ethanol and isopropanol); a ketone (such as a C3-C5 ketone such as acetone); for example. The designations C1-C5 or C3-C5 refer to the number of carbon atoms in the alcohol or ketone. One or more washing steps may be carried out on the fixed cells using a buffered aqueous medium.

If necessary after fixation, the cell preparation is also subjected to permeabilization. In some instances, a fixation agent such as, for example, an alcohol (e.g., methanol or ethanol) or a ketone (e.g., acetone) also results in permeabilization and no additional permeabilization step is necessary. Permeabilization provides access through the cell membrane to antigens of interest. The amount of permeabilization agent employed is that which disrupts the cell membrane and permits access to the antigens. The amount of permeabilization agent depends on one or more of the nature of the permeabilization agent and the nature and amount of the cells, for example. In some examples, the amount of permeabilization agent is about 0.01% to about 10%, or about 0.1% to about 10%, for example. Agents for carrying out permeabilization of the cells include, but are not limited to, an alcohol (such as, e.g., C1-C5 alcohols such as methanol and ethanol); a ketone (such as a C3-C5 ketone such as acetone); a detergent (such as, e.g., saponin, Triton® X-100, and Tween®-20); for example. One or more washing steps may be carried out on the permeabilized cells using a buffered aqueous medium.

In the immunocytochemistry technique, a labeled antibody specific for an antigen on a cell is employed for each suspected different cell population. The labels are fluorescent labels and a different fluorescent label is employed for each different cell population such that multiple fluorescent-labeled antibodies may be employed in any one assay conducted on the material present on a surface of a porous matrix.

The surface of the matrix comprising the different cell populations is contacted with an aqueous medium containing one or more labeled antibodies as described above. The aqueous medium may be an aqueous buffered medium and the amount of each labeled antibody is that which is sufficient to identify each of the different cell populations present on a surface of a porous matrix. In some examples, the amount of each labeled antibody is in excess of the suspected amount of the cells in a cell population. The cells are incubated with the labeled antibodies under conditions that permit binding of the labeled antibodies to their respective antigens of the different cells.

For incubation, moderate temperatures are normally employed and usually constant temperature, preferably, room temperature. Incubation temperatures normally range from about 5° C. to about 99° C. or from about 15° C. to about 70° C., or about 20° C. to about 45° C., for example. The time period for the incubation is about 0.2 seconds to about 24 hours, or about 1 second to about 6 hours, or about 2 seconds to about 1 hour, or about 1 to about 15 minutes, for example. The time period depends on the temperature of the medium and the rate of binding of the various reagents. After incubation, the cell populations on the surface of the porous matrix are subjected to one or more washing steps using an aqueous buffered medium to remove unbound labeled antibodies.

A fluorescent DNA stain such as, for example, 4',6-diamidino-2-phenylindole, propidium iodide, ethidium bromide, SYBR® Green I, VISTRA™ GREEN, SYTO® GREEN, SYBR® Gold, YO-PRO-1™, TOTO-3™, TO-PRO-3™, NUCLEAR-ID™ Red, or Hoechst dye, may be employed to enhance contrast during microscopic examination of the surface of the porous matrix. After staining, one or more washing steps may be carried out on the cells using a buffered aqueous medium. The cells are then examined using a fluorescent microscope and each of the different fluorescent labels is used in the direct detection of a respective cell in the different cell populations.

Alternatively, in the above procedure unlabeled antibodies may be employed and the respective antibodies are detected indirectly employing a specific binding member for each of the respective antibodies where the specific binding members are labeled with a fluorescent label or an enzyme label (such as, e.g., thiol-specific antioxidant (TSA enzyme)), for example. The respective labels of the specific binding members are detected by appropriate means. The specific binding members may be, for example, an antibody specific for each of the respective unlabeled antibodies used for binding to a respective antigen of a cell.

Analysis of Extracted Cells

Cells removed, released and/or collected from a surface of a porous matrix in accordance with the principles described herein may be subjected to further analysis. In some examples, analysis may be directed towards the four main biochemical classes, which are carbohydrates, lipids, proteins, and nucleic acids. Examples of analytic methods include, by way of illustration and not limitation, molecular methods such as next generation sequencing, polymerase chain reaction (PCR), microarray analysis, immunoassay techniques such as, for example, sandwich immunoassays and competitive immunoassays, and standard biochemical methods such as, for example, electrophoresis, chromatography, mass spectroscopy, spectroscopy, microfluidics, and microscopy. The techniques include those described above for identifying the location of specific cells on the surface of a matrix. The isolated cells also may be used for other purposes known in the art.

In some examples, extracted or removed cells can be used to determine biomarkers on the cells. A biomarker is a moiety that facilitates the characterization or identification of a cell type. Proteins, RNA, DNA or cell components, for example, may be measured. Measurement of RNA in cell extracts may be carried out using a sensitive fluorescent nucleic acid stain for quantitating double-stranded DNA (dsDNA) and an ELISA plate reader. Other molecular methods that can be applied include, but are not limited to, RNA expression by microarrays, molecular probes such as b-DNA probes, sequencing, reverse transcription polymerase chain reaction (PCR), and quantitative real-time PCR.

The analysis of biomarkers for a small number of cells (for example, 1 cell to about 10,000 cells, or 1 cell to about 5,000 cells, or 1 cell to about 2,000 cells, or 1 cell to about 1,000 cells) often require an amplification dependent on the DNA or RNA marker. A cell contains about 0.010 ng RNA or about 0.003 ng of genomic DNA. However, many detection methods often require more material. For example, Next Generation Sequences (NGS) require about 150 ng to about 250 ng for the Illumina MISEQ® analyzer (Illumina, Inc., San Diego Calif.) or about 20 µg of material for the Illumina HISEQ® analyzer (Illumina, Inc.). Many such methods exist for the RNA and DNA. Once the material has been amplified, specific mutant and expression can be determined.

Amplification methods for RNA may be employed for analysis of extracted cell materials. Whole transcriptome amplification (WTA) uses reverse transcription polymerase chain reaction (qRT-PCR) with special enzymes and random-priming oligonucleotides to make cDNA and amplify a library of short, overlapping amplimers that are a very faithful representation of total cellular RNA.

Whole genome amplification methods for DNA may be employed in the analysis of extracted cell materials. A Multiple Displacement Amplification (MDA) such as, for example, a REPLI-g® UltraFast kit (Qiagen, Inc., Valencia Calif.) or other commercially available kit may be employed. The MDA method uses DNA polymerase, buffers, and reagents for whole genome amplification. The average product length is typically greater than 10 kilobases (kb), with a range between 2 kb and 100 kb.

Select gene amplification methods for DNA by PCR may be employed in the analysis of extracted cell materials. In this case a primer is used to cover a gene of interest or to cover panels of genes for a given disease state. A multiplexed library preparation of approximately 50 gene for all coding regions (exons) to be amplified such as, for example, a cancer panel for ABL1, EGFR, GNAS, MLH1, RET, MEK1, AKT1, ERBB2, HNF1A, MPL, SMAD4, ALK, ERBB4, HRAS, NOTCH1, SMARCB1, APC, FBXW7, IDH1, NPM1, SMO, ATM, FGFR1, JAK2, NRAS, SRC, BRAF, FGFR2, JAK3, PDGFRA, STK11, CDH1, FGFR3, KDR, PIK3CA, TP53, CDKN2A, FLT3, KIT, PTEN, VHL, CSF1R, GNA11, KRAS, PTPN11, DDR2, CTNNB1, GNAQ, MET, RB1 and HER2. In this approach, successful differentiation of wild type and mutant cell lines may be achieved at as little as >16 cells on a membrane by PCR amplification and sequencing using VERSANT® technology (Bayer HealthCare LLC, Berkeley, Calif.) or TRU-GENE® technology (Bayer HealthCare LLC).

The PCR approach to amplification is limited to specific regions of DNA, but allows a much lower (about 1% to about 0.01%) purity of rare cells to normal cells. This makes the PCR method attractive as secondary amplification method after whole-genome amplification (WGA) or whole transcriptome amplification (WTA). The first amplification (WGA or MTA) generates sufficient materials for detection and the second amplification (PCR) adds specificity to the use of lower DNA/RNA purity in the detection method. In one approach, a cell extract undergoes MDA pre-amplification followed by reverse transcriptase-PCR amplification, fragmentation, library preparation and size selection, cleanup, and finally sequencing.

The quality of the DNA/RNA may be measured after extraction and amplification. The sonication method in accordance with the principles described herein allows material of desired quality while traditional extraction methods lead to low quality. Quality may be measured using, for example, an Agilent 2100 Bioanalyzer (Agilent Technologies, Inc., Palo Alto Calif.), which measures RNA/DNA electrophoretically.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

The following examples further describe the specific embodiments of the invention by way of illustration and not limitation and are intended to describe and not to limit the scope of the invention. Parts and percentages disclosed herein are by volume unless otherwise indicated.

Examples

All chemicals may be purchased from the Sigma-Aldrich Company (St. Louis Mo.) unless otherwise noted.

ABBREVIATIONS $K_3$EDTA=potassium salt of ethylenediaminetetraacetate
WBC=white blood cells
RBC=red blood cells
FITC=fluorescein isothiocyanate
DAPI=4',6-diamidino-2-phenylindole
DABCO=1,4-diazabicyclo[2.2.2]octane
xg=times gravity
min=minute(s)
sec=second(s)
h=hour(s)
μm=micron(s)
mL=milliliter(s)
mg=milligrams(s)
μg=microgram(s)
PBS=phosphate buffered saline (3.2 mM $Na_2HPO_4$, 0.5 mM $KH_2PO_4$, 1.3 mM KCl, 135 mM NaCl, pH 7.4)
mBar=millibar
RT=room temperature
° C.=degrees centigrade
~=about
>=greater than
<=less than Whole blood specimens for testing were prepared by collection of blood from normal subjects lacking any rare cells due to disease. The blood samples (7-10 mL) were collected into VACUTAINER® tubes (Becton, Dickinson and Company, Franklin Lakes N.J.) containing $K_3$EDTA. WBC were about $10^7$ per 10 mL blood and RBC were about $5\times10^{10}$ per 10 mL of blood. Cultured rare cells, which were either cultured cancer cells, endothelial cells or epithelial cells (ATCC Manassas, Va.), were added to the blood samples at a level of 10 cells per 10 mL of blood sample. Therefore, before filtration, the ratio of rare cells to all normal cells was 0.00000002% and the rare cell to WBC ratio was 0.00001%. Fibrin at 0.2 to 10 mg/L was added to some samples in accordance with the principles described herein. In some samples additional paraformaldye at 0.05% by volume of the blood sample was added.

Within one day after storage at 25° C., the blood samples were filtered through a membrane having an average pore size of 8 μm according to a method disclosed in U.S. Patent Application Publication No. 2012/0315664, the relevant portions of which are incorporated herein by reference. During filtration, the sample on the membrane was subjected to a negative mBar, that is, a decrease greater than about −30 mBar from atmospheric pressure. The vacuum applied varied from 1 to −30 mBar as the volume of the sample reduces from during filtration. High pressure drops were allowable dependent on reservoir and sample volume and filtration rate. Just prior to filtration, a sample (7-10 mL) was transferred to a 50 mL FALCON® tube, which was filled to 20 mL with cold PBS. The FALCON® tubes were manually overturned twice and subjected to centrifugation for 10 min, at 400×g at 20° C. The diluted sample was placed into the filtration station without mixing and the diluted sample was filtered through the membrane. Following the filtration, the membrane was washed with PBS, and the sample was fixed with formaldehyde, washed with PBS, subjected to permeabilization using of 0.2% TRITON® X100 in PBS and washed again with PBS.

Cells captured on the membrane were detected with an immunocytochemistry (ICC) procedure based on the binding of specific antibodies to specific proteins or antigens in cells. A blocking buffer of 10% casein in PBS was dispensed on the membrane. After an incubation period of 5 min, the membrane was washed with PBS to block non-specific binding to the membrane. Next, an antibody-conjugate mix was dispensed to the membrane followed by an incubation period of 20 min at RT. The mixture of antibody conjugates (in 10% casein in PBS) included anti-cancer cell antibody (reactive to CK8/18) conjugated to Dy550 at 15 μg/mL, and anti-CD45 antibody (used for WBC) conjugated to Dy650 at 20 μg/mL. The mixture of antibody conjugates can include anti-endothelial cell antibody (reactive to CT105) conjugated to Dy550, or anti-epithelial cell antibody (reactive to EPCAM) conjugated to Dy550 at 15 μg/mL, in place of the anti-cancer cell antibody (reactive to CK8/18) conjugated to Dy550. Unbound antibody was washed away (PBS+0.05% TWEEN® 20) and DAPI (0.8 μg/mL in PBS), a fluorescent DNA stain was added to stain the nuclei of the cells. A last wash step with PBS was performed, followed by cover media to help preserve the fluorescent intensity of the probes. Slides were made with DABCO as a cover slip medium (0.25 g DABCO to 9 mL glycerol and 1 ml 10×PBS).

Slides were then placed on a slide holder of a fluorescent microscope (Leica DM5000 (Leica Microsystems GmbH, Wetzlar, Germany)) where images were captured during the automated scanning of the membrane for each of the fluorescent probes used for detection of targeted cells. Antibody-conjugates became bound to the protein or antigen of a cell, and the fluorescent labels were detected by using a fluorescent microscope with excitation, emission, and cut-off filters specific for each label. Multiple fluorescent labels, each with a different specific antibody, were used to detect multiple antigens or proteins in the isolated cells.

Cells were then characterized by scanning the membrane by fluorescence microscopics conducted with a Leica DM5000 using the filter sets for respective fluorophore labels used in the antibody-conjugates above, namely, FITC, DyLight 550 (ThermoFisher Scientific, Inc., Waltham Mass.), DyLight 650 (ThermoFisher Scientific, Inc.) or DAPI. Enrichment of rare cells achieved was measured by counting the rare cells (either CK or CD105 or EpCAM positive) and comparing to the count of the normal cells remaining on the membrane. RBC were either lysed or passed through the membrane; all normal cells were WBC (CD45 positive).

Cells were then extracted by scanning the membrane by fluorescence microscopics conducted with a Leica DM5000 using the filter sets for respective fluorophore labels used in the antibody-conjugates above, namely, FITC, DyLight 550 (ThermoFisher Scientific, Inc., Waltham Mass.), DyLight 650 (ThermoFisher Scientific, Inc.) or DAPI. Enrichment of rare cells achieved was measured by counting the rare cells (either CK or CD105 or EpCAM positive) and comparing to the count of the normal cells remaining on the membrane. RBC were either lysed or passed through the membrane; all normal cells were WBC (CD45 positive). Cell counts were obtained.

The filtration method allowed >99% reduction of WBC and removed all RBC (See Table 1). For a whole blood sample containing 1000 cancer cells, ratio of WBC to cancer cells decreased from 50,000-100,000/1 to <200/1 (0.5%).

Cancer and endothelial cells were close to 95% cell recovery (measurements ranged from 80 to 120% depending on the replicate).

TABLE 1

Enrichment efficiency of filtration

|  | Whole blood sample (10 mL) | Membrane (25 mm diameter) |
| --- | --- | --- |
| RBC | ~5 × $10^{10}$ | 0 |
| Total WBC | ~5-10 × $10^{7}$ | 50,000-100,000 |
| Rare cells | 1 to 1000 | 95% |

Extractions of cell materials from the membrane were conducted by placing the membrane surface with captured cell down on the top of 300 to 1000 µL of receiving buffer. The receiving buffers used were 50 mM ammonium bicarbonate buffer at pH 7.7 or PBS. In addition, protease inhibitors can be added (Sigma-Aldrich, Sigma Cat S8820) and the buffer can be cooled. An ultrasonic processor (Model Q500, Qsonic, Newtown Conn.) was fitted with a probe. For extraction of the complete membrane, a ½-inch diameter tip was attached to the horn extractor and, for extraction of a small region, a microtip (about 1 mm diameter) was attached to the horn extractor. For the ½-inch diameter tip, the probe was placed over the upwards facing side of the membrane at a distance of 0 to 5 mm and ultrasonic energy was applied to the probe sonicate at a power 20% of 1000 V rms at 20 kHz for 5 sec. In the case of the microtip, the probe was swept over the surface of the entire membrane or was used at a specific location identified to contain cells of interest based on the original microscope scan as discussed above. After cell removal from the membranes, the membranes were scanned by fluorescence microscopy and remaining cells were counted.

For comparison, extractions of cell materials from the membrane were also conducted by the traditional methods of using solutions containing trypsin (2.5% trypsin, Sigma-Aldrich P/N T1426), trypsin plus surfactant (2.5% trypsin, Sigma-Aldrich P/N T1426 plus 0.2% TRITON® X-100, Sigma Aldrich P/N X100PC) or lysis buffer (100% lysis buffer, Calbiochem-Novabiochem Corporation, Billerica, Mass., Calbiochem P/N JA1978 plus 0.2% EDTA (Sigma-Aldrich P/N 4884). Membranes were placed into solution and incubated for 37° C. for 1 h. After cell removal from the membranes, the membranes were scanned by fluorescence microscopy and remaining cells were counted.

The results for the five types of extraction methods (Methods 1-5) are summarized below in Table 2. Method 1 used trypsin. Method 2 used trypsin plus surfactant. Method 3 used lysis buffer. Method 4 used the microtip sonication probe, and method 5 used the ½-inch diameter tip sonication probe. Cell counts for white blood cells (WBC) and rare cells (RC) are shown for membrane before extraction and the percent (%) removal of these cells is shown after application of the method.

TABLE 2

| Method | WBC (Count) | RC (Count) | % WBC Removal | % RC Removal |
| --- | --- | --- | --- | --- |
| 1 | 89951 | 1280 | 0% | 20% |
| 2 | 89900 | 680 | 85% | 97% |
| 3 | 86739 | 540 | 17% | 41% |
| 4 | 114849 | 600 | 100% | 100% |
| 5 | 81117 | 720 | 100% | 100% |

The results are categorized as extraction using Methods 4 and 5, which are in accordance with the principles described herein, and extraction using non-sonication Methods 1-3, which are not in accordance with the principles described herein and are provided for purposes of comparison. Only Methods 4 and 5, the sonication methods in accordance with the principles described herein, removed all cells. Enrichment ratio of 1 to 200 RC/WBC, which was observed on the membrane, was also observed in extracted sample when the large tip in Method 5 was used. Selective removal of regions of interest was demonstrated when the small tip in Method 4 was used. This improved the enrichment ratio of 1 to 10 RC/WBC in the extracted sample. Methods 1-3, the non-sonication methods, were found to leave cells on the membrane as can be seen in Table 2. The use of trypsin also fragmented and damaged biomarker activity of the cells Immunoreactivity of biomarkers on the cells was completely lost or greatly reduced in the extract.

Extracted cells were used to determine biomarkers on the cells. Her2nue from rare cancer cells was measured in cell extracts using a Her2nue ELISA (C-ErbB2/c-neu Rapid Format ELISA Kit, Calbiochem P/N QIA-10). The measurement of a Her2nue in the cell extracts was demonstrated for 2×$10^5$ SKBR cancer cells on the membrane without amplification. The measurement of RNA in the cell extracts was demonstrated for SKBR cancer cells on the membrane without amplification using the RNASCOPE®, a Novel RNA In Situ (Advanced Cell Diagnostics Inc, Hayward Calif.) method ultra sensitive fluorescent nucleic acid stain for quantitating a single RNA molecule in a single cell using a branched DNA probe methodology with direct fluorescent labels. Fluorescent signal observed for RNA for Her2neu in each SKBR cell are imaged by a fluorescent microscope.

Amplification methods for RNA were tested for extracted cell materials. A whole transcriptome amplification (WTA) (see, for example, S. A. Tomlins, et al., Neoplasia 153-162 (2006)) or an OVATION® RNA-Seq System (NuGen Technologies, Inc., San Carlos Calif.) was employed. Experiments showed that picogram (pg) quantities of total RNA yield 2.6 µg of cDNA in good quality in 5 hours from about 50 target cells. The amplified cDNA can be used for qPCR analysis and storage for future use.

Whole genome amplification methods for DNA were tested for extracted cell materials. A Multiple Displacement Amplification (MDA) (REPLI-g® UltraFast (Qiagen, Inc., Valencia Calif.) according to the instructions of the manufacturer. The DNA concentration of the WGA products was measured with QUANT-iT™ assays (Invitrogen Life Science, Inc., Grand Island N.Y.) according to the manufacturer's instruction. Experiments showed that 50 µg of DNA in good quality was obtained from about 300 target cells.

Select gene amplification methods for DNA by polymerase chain reaction (PCR) was tested for extracted cell materials. In this case a primer is used to cover a gene of interest or to cover panels of genes for a given disease state. A multiplexed library preparation of approximately 50 gene for all coding regions (exons) to be amplified such a cancer panel for ABL1, EGFR, GNAS, MLH1, RET, MEK1, AKT1, ERBB2, HNF1A, MPL, SMAD4, ALK, ERBB4, HRAS, NOTCH1, SMARCB1, APC, FBXW7, IDH1, NPM1, SMO, ATM, FGFR1, JAK2, NRAS, SRC, BRAF, FGFR2, JAK3, PDGFRA, STK11, CDH1, FGFR3, KDR, PIK3CA, TP53, CDKN2A, FLT3, KIT, PTEN, VHL, CSF1R, GNA11, KRAS, PTPN11, DDR2, CTNNB1, GNAQ, MET, RB1 and HER2. To demonstrate the principle, DNA sequences for kRAS using PCR amplification of KRAS Codon 12 and 13 using primers. In this example, successful differentiation of kRAS wild type and mutant cell lines at as little as >16 cells on a membrane by PCR amplification and sequencing using either VERSANT® technology or TRUGENE® technology was demonstrated.

The PCR approach to amplification is limited to specific regions of DNA, but allows a much lower (1% to 0.01%) purity of rare cells to normal cells. This makes the PCR method attractive as secondary amplification method after WGA or WTA. The combination allowed detection of DNA at 0.01% purity (10 rare cells in 100,000 WBC) starting with 30 μg DNA/RNA (10 cells).

The quality of the DNA/RNA was measured after extraction and amplification. Using the sonication method in accordance with the principles described herein allowed material of desired quality to be obtained while the traditional extraction methods lead to low quality material. Quality was measured by Agilent's 2100 Bioanalyzer, which measures RNA/DNA electrophoretically.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method of releasing particles from a selected particle-containing area of a first surface of a matrix, the method comprising contacting the selected particle-containing area with a liquid collection medium and selectively applying sonic energy to an opposing area on a second surface of the matrix to release the particles from the selected particle-containing area while particles in non-selected areas of the matrix remain attached on the first surface, wherein the opposing area is opposite to the selected particle-containing area, wherein the matrix is a porous matrix configured for particles to pass through the porous matrix having a pore size of about 1 μm to about 100 μm.

2. The method according to claim 1 wherein the liquid collection medium is an aqueous buffered medium.

3. The method according to claim 1 wherein the sonic energy is selectively applied by means of an ultrasonic probe.

4. The method according to claim 1 wherein the frequency of the sonic energy applied is about 20 kHz to about 200 MHz for a period of about 1 second to about 30 minutes.

5. The method according to claim 1 further comprising subjecting the released particles to analysis.

6. The method according to claim 1 wherein the particles are biological particles.

7. The method according to claim 1 wherein the matrix is disposed over a container that contains the liquid collection medium.

8. The method according to claim 1, wherein the pore size is about 1 μm to about 10 μm.

9. A method of selectively collecting a population of biological particles from a surface of a porous matrix comprising different biological particle populations, the method comprising for each different biological particle population to be collected:
  (a) selectively applying sonic energy to an opposing area on a first surface of the porous matrix wherein the opposing area corresponds to a selected area on a second surface of the porous matrix wherein the selected area on the second surface comprises the population of biological particles to be selectively collected, wherein the matrix is a porous matrix configured for particles to pass through the porous matrix having a pore size of about 1 μm to about 100 μm, and
  (b) selectively collecting the biological particles of the population of biological particles from the selected area on the second surface into a liquid collection medium in contact with the selected area on the second surface, and wherein the different biological particle populations in non-selected areas on the second surface remain intact on the porous matrix surface until selected.

10. The method according to claim 9 wherein the liquid collection medium is an aqueous buffered medium.

11. The method according to claim 9 wherein the sonic energy is selectively applied by means of an ultrasonic probe.

12. The method according to claim 9 wherein the frequency of the sonic energy selectively applied is about 20 kHz to about 200 MHz for a period of about 1 second to about 30 minutes.

13. The method according to claim 9 further comprising subjecting the selectively collected biological particles to analysis employing polymerase chain reaction, whole genome amplification and polymerase chain reaction, whole transcriptome amplification and polymerase chain reaction, RNA amplification or an immunoassay.

14. The method according to claim 9 wherein the biological particles are cells.

15. The method according to claim 9 wherein the porous matrix is disposed over a container that contains the liquid collection medium.

16. The method according to claim 9, wherein the pore size is about 1 μm to about 10 μm.

17. A method of selectively collecting a population of cells from a surface of a porous matrix comprising different cell populations, the method comprising for each different cell population to be collected:
  (a) selectively applying sonic energy having a frequency of about 20 kHz to about 200 MHz to an opposing area on a first surface of the porous matrix wherein the opposing area corresponds to a selected area on a second surface of the porous matrix wherein the selected area on the second surface is identified as comprising the population of cells to be selectively collected, and wherein a pore size of the porous matrix configured for particles to pass through the porous matrix is about 1 μm to about 100 μm, and
  (b) selectively collecting cells of the population of cells from the selected area on the second surface into an aqueous buffered medium in contact with the selected area on the second surface wherein the porous matrix is disposed over a container that contains the aqueous buffered medium, and wherein the different cell populations in non-selected areas on the second surface remain intact on the porous matrix surface until selected.

18. The method according to claim 17 wherein the population of cells of the opposing area is identified by a cell staining technique.

19. The method according to claim 17 wherein the cells are rare cells present in an amount of about $10^{-8}$% to about $10^{-2}$% by weight of the total cell population of said porous matrix.

20. The method according to claim 17 wherein the sonic energy is selectively applied by means of an ultrasonic probe.

21. The method according to claim 17, wherein the pore size is about 1 μm to about 10 μm.

* * * * *